(12) United States Patent
Martin et al.

(10) Patent No.: US 6,818,791 B2
(45) Date of Patent: Nov. 16, 2004

(54) METHOD FOR PRODUCING HIGHER (METH)ACRYLIC ACID ESTERS

(75) Inventors: Friedrich-Georg Martin, Heidelberg (DE); Gerhard Nestler, Ludwigshafen (DE); Jürgen Schröder, Lugwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/450,438

(22) PCT Filed: Dec. 17, 2001

(86) PCT No.: PCT/EP01/14902
§ 371 (c)(1),
(2), (4) Date: Jun. 18, 2003

(87) PCT Pub. No.: WO02/50014
PCT Pub. Date: Jun. 27, 2002

(65) Prior Publication Data
US 2004/0024241 A1 Feb. 5, 2004

(30) Foreign Application Priority Data
Dec. 18, 2000 (DE) .......................................... 100 63 175

(51) Int. Cl.⁷ .............................................. C07C 69/52
(52) U.S. Cl. ....................................................... 560/205
(58) Field of Search ......................................... 560/205

(56) References Cited

U.S. PATENT DOCUMENTS 2,917,538 A    12/1959  Cartyle et al.
4,053,504 A    10/1977  Rosenkranz et al.

FOREIGN PATENT DOCUMENTS

| DE | 1 067 806  | 10/1959 |
| DE | 14 93 004  | 1/1969  |
| DE | 20 50 678  | 4/1972  |
| DE | 28 38 691  | 3/1979  |
| DE | 29 13 218  | 10/1980 |
| DE | 196 04 253 | 8/1997  |
| EP | 0 618 187  | 10/1994 |
| WO | 90 07487   | 7/1990  |
| WO | 97 37962   | 10/1997 |

OTHER PUBLICATIONS

Ullmann's Encyclopedia of Industrial Chemistry, vol. A1, pp. 162–169 1985.

*Primary Examiner*—Paul J. Killos
(74) *Attorney, Agent, or Firm*—Oblon, Spivak, McClelland, Maier & Neustadt, P.C.

(57) ABSTRACT

The invention relates to a method for producing (meth) acrylic acid esters by transesterification of the (meth)acrylic acid with a higher alkanol in the presence of an acid catalyst, at least one polymerization inhibitor and one organic solvent that forms an azeotropic mixture with water. The reaction mixture is heated to the boiling point of the mixture in a reactor that comprises a distillation unit with a column and a condenser. The content of the reactor is recirculated via an external evaporator and heated to the boiling point, and the azeotropic mixture is distilled off. The organic solvent forms a reflux and at least a part of the solvent reflux is recirculated between the reactor and the evaporator. The inventive method allows for the production of higher (meth)acrylic acid esters in a reactor with a circulation evaporator without using copper salts as the polymerization inhibitors.

7 Claims, 1 Drawing Sheet

METHOD FOR PRODUCING HIGHER (METH)ACRYLIC ACID ESTERS

Figure 1:
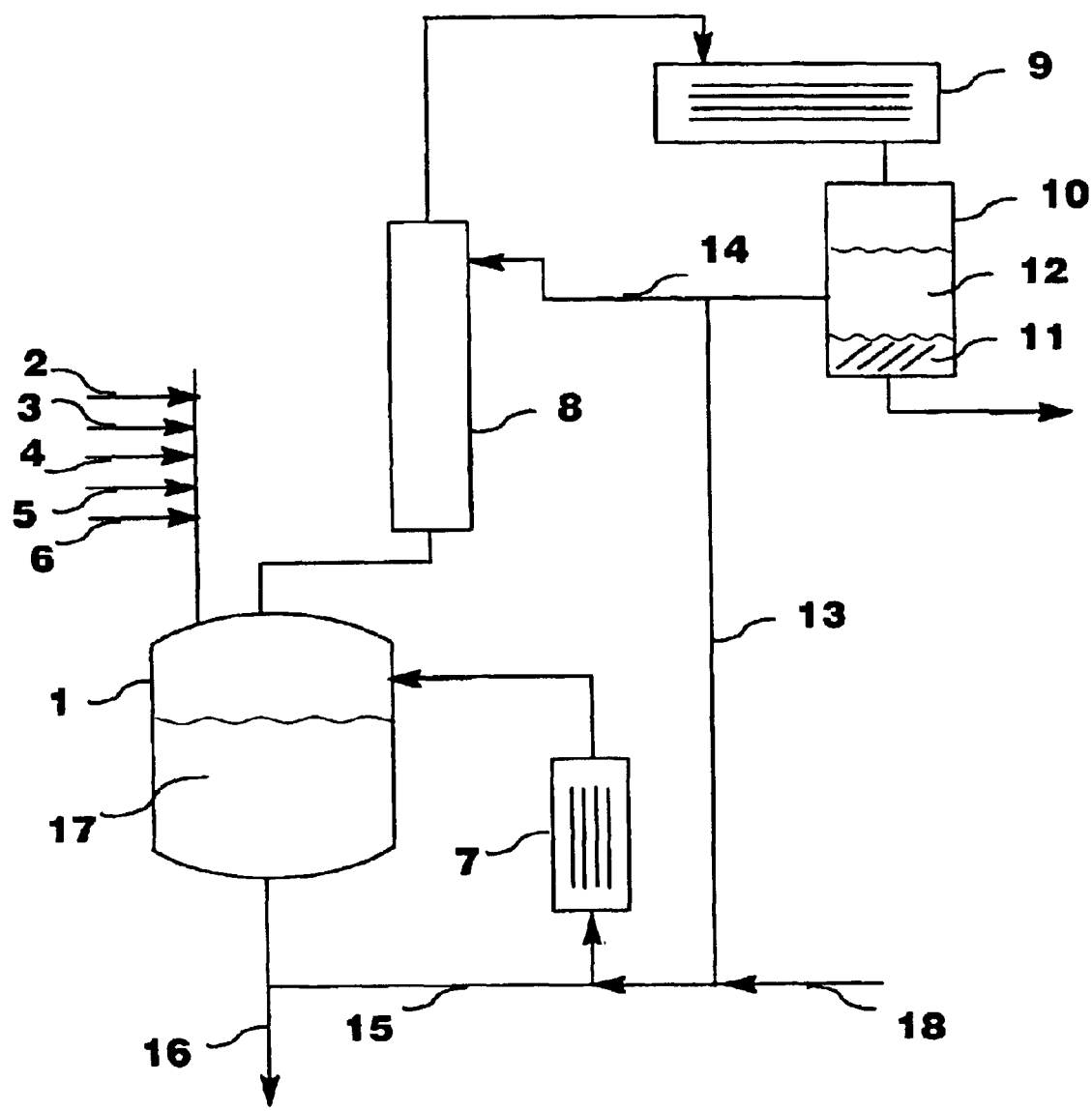

The present invention relates to a process for the preparation of higher (meth)acrylates by esterifying (meth)acrylic acid (acrylic acid, methacrylic acid) with an alkanol.

(Meth)acrylates are useful starting compounds for the preparation of polymers and copolymers which are used, for example, as surface coatings, dispersions or adhesives. The preparation of (meth)acrylate by acid-catalyzed esterification of (meth)acrylic acid with alkanols is generally known, cf. for example Ullmann's Encyclopedia of Industrial Chemistry, Vol. A1, 162-169, VCH 1985. The formation of the ester from (meth)acrylic acid and alkanol is known to be based on an equilibrium reaction. In order to obtain economical conversions, as a rule one starting material is used in excess and/or the resulting water of esterification is removed from the equilibrium. In order to accelerate and facilitate the removal of the water, an organic solvent which is immiscible with water or forms an azeotropic mixture with water is generally added. Frequently used solvents are aliphatic, cycloaliphatic and/or aromatic hydrocarbons, such as pentanes, hexanes, heptanes, cyclohexane or toluene, cf. for example DE 20 50 678 A, DE 29 13 218 A, U.S. Pat. No. 4,053,504 A, U.S. Pat. No. 2,917,538 A and EP 618 187 A.

A major problem in the esterification of (meth)acrylic acid is the high tendency of the (meth)acrylate compounds to polymerize owing to their reactive double bonds. This is true in particular if the (meth)acrylate compounds are exposed to relatively high temperatures, cf. for example WO 97/37962. In their preparation and the distillative purification, (meth)acrylate compounds are exposed to temperatures which can readily trigger undesired polymerization and can lead to polymer formation. This results in soiling of the apparatuses, blockage of pipes and pumps and coating of column trays and heat exchanger surfaces (fouling). The cleaning of the equipment is a complicated, expensive and presents environmental problems, cf. DE 10 67 806 A. In addition, yield and plant availability are greatly reduced thereby.

As a rule, polymerization inhibitors, i.e. compounds which are capable of substantially suppressing the free radical polymerization, are therefore added for stabilization. For the use of the (meth)acrylate compounds, however, the polymerization inhibitors have to be separated off. In the preparation of high-boiling (meth)acrylate compounds which cannot be purified by distillation, it is possible to use only inhibitors which can be separated off by another method, for example by extraction, filtration or adsorption, or which do not interfere with the further processing. Thus, DE 28 38 691 A describes the use of Cu(I) oxide as an inhibitor, the Cu(I) oxide being removed by extraction. WO 90/07487 describes the use of hydroquinone with addition of active carbon to the esterification mixture. The active carbon, which is filtered off after the esterification, is added during the esterification in order to avoid discoloration of the ester due to the hydroquinone. DE 29 13 218 A discloses the use of phosphites, such as triethyl phosphite, as a polymerization inhibitor.

The esterification of (meth)acrylic acid is generally effected in a reactor to which a distillation column having a condenser is attached, said column serving to remove from the reactor the water in the form of the azeotropic mixture with the solvent. Frequently used reactors are stirred reactors having double-wall heating. The disadvantage here is that the stirrers frequently need to be repaired and polymer readily accumulates on them. Moreover, the reactor size is subject to limits because the specific wall area available for heat transfer decreases with increasing reactor size.

Circulation evaporators are also frequently used as reactors for the preparation of (meth)acrylates. Although said problems do not occur, it is necessary to add very efficient polymerization inhibitors, for example copper salts, during the esterification. The copper salts have to be removed from the (meth)acrylates by washing out with water. The wash water must be disposed of, i.e. either it pollutes the wastewater or the copper salts have to be removed from the wash water by an expensive procedure, for example with the aid of ion exchangers, electrolysis cells, etc.

It is an object of the present invention to provide a process for the preparation of higher (meth)acrylates which is carried out in a reactor having an external circulation evaporator and in which the polymer formation is suppressed.

We have found, surprisingly, that this object is achieved if at least some of the reflux is passed into the circulation evaporator during the esterification with heating to the boiling point.

The present invention relates to a process for the preparation of higher (meth)acrylates by esterifying (meth)acrylic acid with a higher alkanol in the presence of at least one acidic catalyst, at least one polymerization inhibitor and an organic solvent which forms an azeotropic mixture with water, with heating in a reactor having a distillation unit, which comprises a column and a condenser, to the boiling point of the reaction mixture, wherein the reactor content is circulated via an external evaporator and is heated to the boiling point, and the azeotropic mixture is distilled off, the organic solvent present in the azeotropic mixture forming the reflux, and at least some of the solvent reflux being passed into the circulation between reactor and evaporator.

The mode of operation used according to the invention for reactor and evaporator constitutes circulation evaporation. The evaporator is thus referred to below as a circulation evaporator.

According to the invention, the esterification is carried out in one or more reactors connected in series and having an external circulation evaporator. It is possible to use a forced-circulation evaporator with a pump as a circulation system. However, a natural circulation evaporator in which the circulation is produced without mechanical aids is preferably used. Suitable circulation evaporators are known to a person skilled in the art and are described, for example, in R. Billet, Verdampfertechnik, HTB-Verlag, Bibliographisches Institut Mannheim, 1965, 53. Examples of circulation evaporators are tube-bundle heat exchangers, plate-type heat exchangers, etc.

In order to carry out the esterification, the starting materials are introduced into the reactor. The reaction mixture is heated to the boil with the aid of the circulation evaporator, and the water formed during the esterification is distilled off as an azeotropic mixture with the organic solvent. This is effected via a distillation column and a condenser. Distillation columns of conventional design which have internals having a separation effect, for example, bubble, sieve or dual-flow trays or dumped or stacked packings, are used. A distillation column having dumped packing is preferably used. The packing elements may be of conventional design, for example Raschig, Intos or Pall rings, barrel or Intalox saddles, Top-Pak, etc., cf. also Ullmann's Encyclopedia of Industrial Chemistry, Vol. B3, 4-71 to 4-84, VCH 1988.

The condensers are also of known design and may be, for example, tubular or plate-type heat exchangers. They are preferably operated using water or brine.

The azeotropic mixture of the water formed and the organic solvent is separated off via the distillation column and then condensed in the condenser, the condensate separating into an aqueous phase and an organic phase and being collected in a separation container. The aqueous phase is at least partly discharged or can be further processed to recover the (meth)acrylic acid contained therein. The organic phase is the reflux which is at least partly passed into the circulation between reactor and circulation evaporator. Preferably, at least 10% by weight, in particular at least 25% and particularly preferably at least 40%, of the reflux are passed into the circulation. The reflux is preferably fed into the pipe leading from the reactor to the circulation evaporator and forming the feed to the circulation evaporator or alternatively into the circulation evaporator in the region of the feed. After passing through the circulation evaporator, the reaction mixture is recycled to the reactor. Some of the organic phase can be passed as reflux into the head of the distillation column (in general about 20 to 60% of the organic phase).

The novel process is suitable for the preparation of esters of (meth)acrylic acid with higher alkanols. However, it can preferably be used for the preparation of higher (meth) acrylates which have a molecular weight of >200 or a boiling point at standard pressure of $\geq 200°$ C., in particular >250° C. Such esters in general cannot be purified by distillation. Useful alkanols include monoalcohols and polyalcohols. The following alcohols are preferably used:

- $C_8$–$C_{20}$-monoalcohols, such as 2-ethylhexyl, 2-propylheptyl, lauryl or stearyl alcohol;
- $C_1$–$C_4$-alkyl-substituted cyclopentanols and cyclohexanols, such as tert-butylcyclohexanol;
- $C_2$–$Cl_{12}$-diols, such as ethylene glycol, 1,2- and 1,3-propylene glycol, 1,2, 1,3- or 1,4-butylene glycol, 1,6-hexanediol, etc., and their mono-$C_1$–$C_4$-alkyl ethers;
- polyethylene glycols and polypropylene glycols, such as diethylene glycol, triethylene glycol, tetraethylene glycol, dipropylene glycol, tripropylene glycol, etc., and their mono-$C_1$–$C_4$-alkyl ethers;
- triols and higher polyols, such as glycerol, trimethylolpropane, pentaerythritol, etc., or the $C_1$–$C_4$-alkyl ethers thereof having at least one free hydroxyl group;
- cyclic trimethylolpropane formal (5-ethyl-5-hydroxymethyl-1,3-dioxolane)
- the ethoxylated and/or propoxylated derivatives of said alcohols.

The ratio of the number of equivalents of alkanol to the number of equivalents of (meth)acrylic acid is in general from 1:0.7 to 1:2.

A preferably used acidic esterification catalyst is p-toluenesulfonic acid. Other esterification catalysts which may be used are organic sulfonic acids, e.g. methanesulfonic acid, benzenesulfonic acid or dodecylbenzenesulfonic acid, and/or sulfuric acid, which is preferred. The esterification catalyst is used in general in an amount of from 0.1 to 10, preferably from 0.5 to 5, % by weight, based on (meth)acrylic acid and alkanol.

The polymerization inhibitors used are conventional inhibitors, such as hydroquinone, hydroquinone monomethyl ether, 2,6-di-tert-butyl-4-methylphenol, 2,4-di-tert-butyl-6-methylphenol, tert-butylpyrocatechol, p-benzoquinone, p-nitrosophenol, phenothiazine or N-oxyl compounds, such as 4-hydroxy-2,2,6,6-tetramethyl-1-oxylpiperidine, or mixtures thereof. The inhibitors are used as a rule in an amount of from 200 to 2 000 ppm, based on (meth)acrylic acid and alkanol. They can be used with addition of air or oxygen-containing gas mixtures if required.

Suitable organic solvents are those which form an azeotropic mixture with water. Aliphatic, cycloaliphatic and/or aromatic hydrocarbons, such as pentanes, hexanes, heptanes, cyclohexane or toluene, are preferably used. The solvent is used in general in an amount of from 5 to 50% by weight, based on the reaction mixture.

The esterification is carried out at elevated temperature. The reaction temperature is in general from 60 to 160° C., preferably from 80 to 130° C. The reaction time is in general from 1 to 20, preferably from 2 to 10, hours. The pressure is not critical and it is possible to use reduced, superatmospheric or preferably ambient pressure.

After the esterification, the reaction mixture is expediently subjected to extraction with water and/or with an aqueous alkali or alkaline earth solution. The organic solvent is then distilled off via a distillation column. The (meth) acrylate, together with the catalyst and the inhibitor, remains as a residue and can be further purified, as described, for example, in Ullmann's Encyclopedia of Industrial Chemistry, Vol. A1, 168-169, VCH 1985. For example, the acidic esterification catalyst, residual (meth)acrylic acid and any inhibitor can be removed by extraction with water. The crude ester can then be subjected to steam stripping to remove residual solvent.

The novel process has the advantage that it can be carried out using simple reaction containers without moving parts. In addition, the process is flexible with regard to the reactor size. The process takes place in a gentle manner and with reduced polymer formation. The use of copper salts as inhibitors is therefore not necessary, so that there is also no need for them to be extracted with water in order to put the (meth)acrylate to further use. Furthermore, the conversion is improved.

The novel process can be used not only for the preparation of methacrylates but also for the preparation of esters of other α,β-ethylenically unsaturated carboxylic acids, such as crotonic acid, itaconic acid, maleic acid, fumaric acid or citraconic acid, with alkanols and in particular the above-mentioned alkanols.

The novel process is explained below with reference to FIG. 1.

FIG. 1 schematically shows an apparatus for carrying out the process and the process sequence. A container without moving parts is used as reactor 1. The starting materials (meth)acrylic acid, alkanol, catalyst, organic solvent and polymerization inhibitor are introduced into the reactor 1 via the lines 2 to 6. The reaction mixture 17 is circulated and heated via line 15 via the circulation evaporator 7, which is in the form of a tube-bundle evaporator. The solvent used or the azeotropic mixture of the water formed in the esterification and the solvent is separated off via the distillation column 8. The vapors are condensed in the condenser 9 and collected in the separation container 10. In the separation container 10, the condensate separates into a lower aqueous layer 11 and an upper organic layer 12, which substantially comprises the organic solvent used. The aqueous layer 11 is at least partly discharged from the process and can be further worked up to recover the (meth)acrylic acid contained in the aqueous layer.

The upper organic layer is fed via line 13 into the line 15 between reactor and circulation evaporator 7. If desired, fresh solvent is added via line 18. If required, a part of the upper organic layer 12 is added as reflux to the distillation column 8 via line 14. After the end of the esterification, the reaction product obtained is removed from the reactor 1 via line 16 and is further worked up.

EXAMPLE 1

172 g of (meth)acrylic acid, 9.2 g of methoxyphenol, 0.3 g of phenothiazine, 23.8 g of 50% strength phosphinic acid, 497 g of 65% strength p-toluenesulfonic acid and 1 030 g of cyclohexane were initially taken in a 10 l reactor having an external natural circulation evaporator, distillation column, condenser and separation container (phase separator). The natural circulation evaporator was a tube-bundle heat exchanger heated by means of heat-transfer oil. Said heat exchanger consisted of three tubes, each tube having a length of 700 mm and a diameter of 9 mm. The forward flow temperature of the heat-transfer oil was 150° C. and the oil circulation was manually regulated. In addition, air was passed into the natural circulation evaporator, the air flow rate being 4 l/h. The distillation column had a diameter of 50 mm and a length of 700 mm and was filled with 8 mm glass rings. After the water initially taken with the starting materials had evaporated, a mixture of 344 g of (meth) acrylic acid and 6 000 g of methylpolyethylene glycol (average molecular weight 4 000 g/mol) was metered in. The cyclohexane reflux was metered from below into the natural circulation evaporator and was regulated by means of the internal reactor temperature. The minimum reflux was 1600 g/h. The reaction temperature was increased to 120° C. in the course of 80 minutes. After an esterification time of 330 minutes, the experiment was terminated. Altogether, 207 g of aqueous phase were discharged and 6890 g of crude ester were obtained. The discharged aqueous phase contained 2.6% of (meth)acrylic acid. The crude ester contained 5.4% of (meth)acrylic acid.

COMPARATIVE EXAMPLE 1

Example 1 was repeated. The metering of air into the natural circulation evaporator was increased to 30 l/h. The cyclohexane reflux was metered via the head of the distillation column into the reactor.

The reactor content had polymerized after an esterification time of 80 minutes.

Example 1 and comparative example 1 show that the novel process prevents polymerization during operation without copper salts.

EXAMPLE 2

The apparatus used was the same as that in example 1. 2 920 g of dipropylene glycol, 3.2 g of methoxyphenol, 6.4 g of 50% strength phosphinic acid, 311 g of 65% strength p-toluenesulfonic acid and 1 730 g of cyclohexane were initially taken. The natural circulation evaporator was a tube-bundle heat exchanger heated by means of heat-transfer oil. The tube-bundle heat exchanger consisted of three tubes, each tube having a length of 700 mm and a diameter of 9 mm. The forward flow temperature of the heat-transfer oil was 150° C. and the oil circulation was manually regulated. In addition, air was passed into the natural circulation evaporator, the air flow rate being 2 l/h. The distillation column had a diameter of 50 mm and a length of 700 mm and was filled with 8 mm glass rings. After the initially taken mixture circulated in the evaporator, 3 240 g of acrylic acid were metered in. The cyclohexane reflux was divided, 800 g/h being metered from below into the natural circulation evaporator and the remaining amount being pumped as reflux to the distillation column and regulated by means of the internal reactor temperature. The minimum reflux of the distillation column was 1 600 g/h. The reaction temperature was increased to 95° C. in the course of 120 minutes. After an esterification time of 510 minutes, the experiment was terminated. Altogether, 933 g of aqueous phase were discharged and 7 000 g of crude ester were obtained. The discharged aqueous phase contained 8.9% of acrylic acid. The crude ester contained 6.2% of acrylic acid. The discharged amount of water corresponded to 94% of theory.

COMPARATIVE EXAMPLE 2

Example 2 was repeated. In addition, 11.6 g of 18% strength copper sulfate solution were initially taken. No cyclohexane was metered into the natural circulation evaporator.

After an esterification time of 510 minutes, the experiment was terminated. Altogether, 822 g of aqueous phase were discharged and 6 990 g of crude ester were obtained. The discharged aqueous phase contained 7.4% of acrylic acid. The crude ester contained 7.9% of acrylic acid. The discharged amount of water corresponded to 82% of theory.

Example 2 and comparative example 2 show that the novel process improves the conversion.

We claim:

1. A process for the preparation of higher (meth)acrylates comprising:

esterifying (meth)acrylic acid with a higher alkanol in the presence of at least one acidic catalyst, at least one polymerization inhibitor and an organic solvent which forms an azeotropic mixture with water and which is selected from the group consisting of aliphatic, cycloaliphatic and aromatic hydrocarbons, heating in a reactor having a distillation unit, which comprises a column and a condenser, to the boiling point of the reaction mixture, wherein the reactor content is circulated via an external evaporator and is heated to the boiling point, and the azeotropic mixture is distilled off, the organic solvent present in the azeotropic mixture forming the solvent reflux, and at least some of the reflux being passed into the circulation between reactor and evaporator.

2. A process as claimed in claim 1, wherein the solvent reflux is passed completely into the circulation evaporator.

3. A process as claimed in claim 1, wherein the solvent reflux is passed into the feed to the circulation evaporator or directly into the circulation evaporator in the region of the feed.

4. A process as claimed in claim 1, wherein a natural circulation evaporator is used.

5. A process as claimed in claim 1, wherein an alkanol which gives a (meth)acrylate having a molecular weight of >greater than 200 is used.

6. A process as claimed in claim 5, wherein the alkanol is selected from the group consisting of lauryl alcohol, stearyl alcohol, tert-butylcyclohexanol, ethyldiglycol, cyclic trimethylolpropane formal 1,6-hexanediol, a polyethylene glycol or polypropylene glycol, a $C_1$–$C_4$-monoalkyl ether thereof, a polypropylene glycol, a $C_1$–$C_4$-monoalkyl ether thereof, glycerol, trimethylolpropane, pentaerythritol and the ethoxylated or propoxylated compounds thereof.

7. A process as claimed in claim 2, wherein the solvent reflux is passed into the feed to the circulation evaporator or directly into the circulation evaporator in the region of the feed.

\* \* \* \* \*